Figure 1:
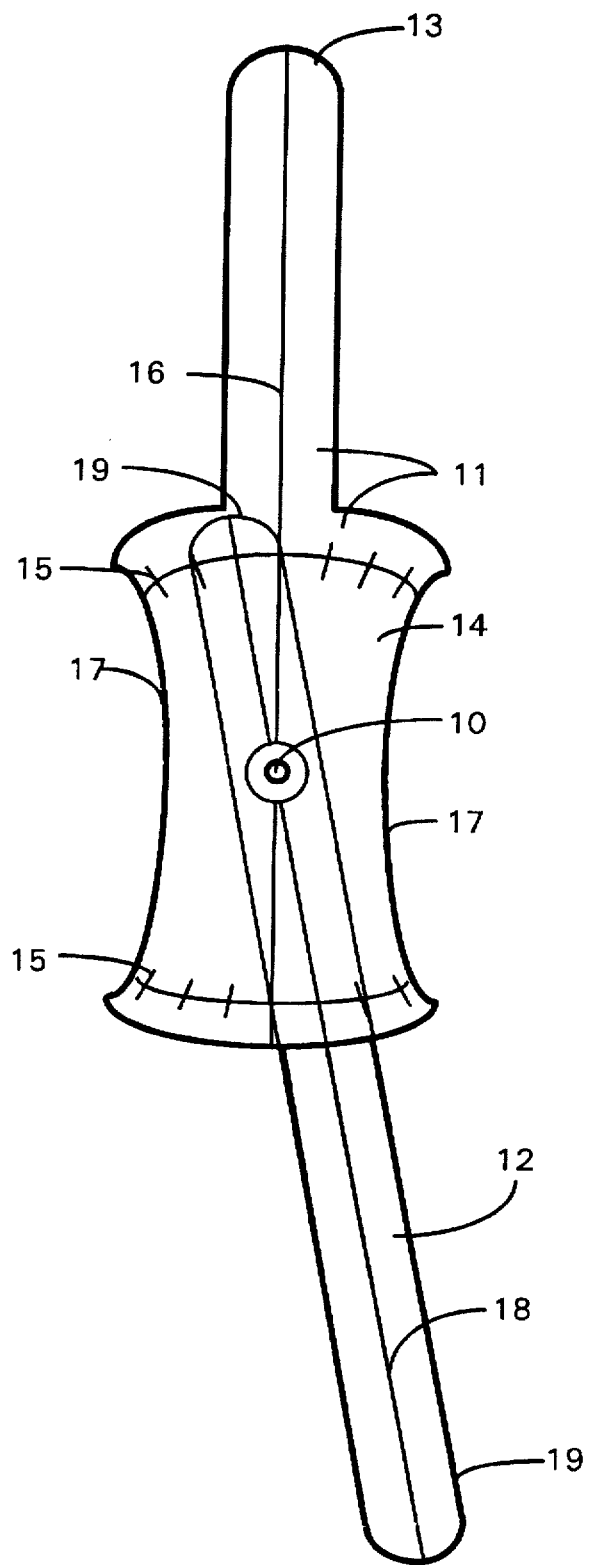

United States Patent [19]

Stefanakos

[11] Patent Number: 5,678,317

[45] Date of Patent: Oct. 21, 1997

[54] METHOD FOR MEASURING LABIAL/FACIAL FLACCIDITY

[76] Inventor: Karlene Stefanakos, 5110 E. Longboat Blvd. E., Tampa, Fla. 33615

[21] Appl. No.: 649,036

[22] Filed: May 16, 1996

[51] Int. Cl.⁶ .................... A61B 5/103; G01B 3/56
[52] U.S. Cl. .................. 33/512; 128/774; 128/778; 606/119
[58] Field of Search ................ 33/512, 511, 1 N; 128/778, 774; 606/1, 119; 1/534

[56] References Cited

U.S. PATENT DOCUMENTS

| | | | |
|---|---|---|---|
| 4,776,347 | 10/1988 | Matthews | 128/774 |
| 5,163,228 | 11/1992 | Edwards et al. | 33/512 |
| 5,186,180 | 2/1993 | Bellas | 33/512 |
| 5,188,120 | 2/1993 | White et al. | 33/512 |

*Primary Examiner*—Christopher W. Fulton

[57] ABSTRACT

A method for measuring labial/facial flaccidity, commonly known as a labial/lip, or facial droop. The method includes the use of a labial goniometer, a hand held device, composed of two flat shanks which are joined in the middle by a grommet that serves as a pivot point. The pivot point allows the shanks to be rotated relative to one another. One shank has a double flare/straight edge and the other a double straight edge. The shank with the double flare is calibrated in degrees, over the range of 0° to 30°, above and below a middle reference centerline that runs longitudinally along the entire length of the shank. This design allows for thirty degree measured movement from the centerline of the flared shank in either direction of rotation from the pivot point. With a patient sitting vertically erect, the curved portion of the flared shank is placed horizontally along the labial/lip seal line, directly under the upper lip tubercle and perpendicular to the philtrum. The labial goniometer's circular grommet is placed in direct alignment to the central philtrum, but under the upper lip tubercle. The reference line on the straight edge shank is used to measure the degree of facial droop by adjusting the shank with the double straight edge upward or downward over the degree range. The measurement of labial/facial flaccidity can be made on either side of the patient's labial facial area.

5 Claims, 1 Drawing Sheet

METHOD FOR MEASURING LABIAL/ FACIAL FLACCIDITY

BACKGROUND OF THE INVENTION

1. Field of The Invention

This invention relates to a method for measuring labial/ facial flaccidity, commonly known as a labial/lip, or facial droop, with patients who have suffered neuromuscular impairment as a result of a stroke, or other impairing diseases which affects the labial/facial neuromuscular integrity. The method includes the use of the labial goniometer. The method may be used in the professions of: speech pathology, medicine (physicians, nursing) occupational therapists, physical therapists, dieticians, respiratory therapists, and recreational therapists.

2. Description of The Prior Art

It is currently a very difficult task to test the positive or negative effects of most therapy treatment. New drug treatments can be readily tested by controlled clinical trials which comprise active treatment compared to a placebo treatment. With few exceptions there have been no adequately controlled trials of remedial therapy, physiotherapy, occupational therapy or speech therapy because the positive or negative results of the therapy are somewhat subjective in nature, and how could one be positive that the same results would have occurred if no therapy were given. Further, unlike drug treatments therapists do not normally condone the practice of not providing therapy to someone who needs it. So it is very unlikely that therapists would agree to having a controlled group, who although needing therapy, was not given it just to complete a clinical trial to test the effectiveness of a therapy method.

However, there are a few methods available to measure the effectiveness of therapy treatments. For stroke victims who have problems walking, gait charts have been developed to examine the walking problems of different subjects using bio-engineering equipment called the polarized light goniometer. For victims who have facial neuromuscular damage, there has to date not been a method of measuring the facial droop of a subject. A method is needed to measure the facial droop or labial/lip droop/flaccidity of an individual who has suffered neuromuscular impairment to facial muscles. With a precise method of measuring labial/lip, the effectiveness of various therapy treatment techniques may be assessed.

SUMMARY OF THE INVENTION

I have invented an economical device, which I call a labial goniometer, that can be used to accurately measure the labial/lip flaccidity of a patient who has facial neuromuscular impairment. The design of the labial goniometer is composed of two flat shanks which are joined in the middle with a grommet which acts as a pivot point. The pivot point allows the shanks to rotate relative to one another. One shank of the labial goniometer has a double flare/straight edge design and the other shank has a double straight edge design along its complete length.

On the shank with the flare design, one longitudinal end has a straight edge design on each side of the shank and the other end is double flared and has a concave curvature on each side of the shank, between the flared portions. The flare side and the straight edge side make up about fifty percent of the total length of the shank. The side of the shank that has a straight edge design is straight on both sides of the shank and is rounded at the end. On the end with the flare design, each flare segment is calibrated in degrees, over the range of zero to thirty degrees, above and below a middle reference centerline that runs longitudinally along the entire length of the shank. The degree ranges are progressive in increments of one degree which provides for accurate measurements of labial/lip flaccidity. The design allows for a total measurement of sixty degrees, thirty degree measured movement from the centerline of the flared shank in either direction of rotation from the pivot point. The side of the shank that is flared on both sides has a circular curve on the end like a segment of a circle. The shank with the double straight edge along its complete length also has a reference centerline that runs longitudinally along the shank. Both longitudinal ends of this shank are rounded.

The curved portion of the flared shank is placed, with a patient sitting vertically erect, horizontally along the labial/ lip seal line directly under the upper lip tubercle and in a perpendicular position to the philtrum. The labial goniometer's circular grommet should be in direct alignment to the central philtrum, but under the upper lip tubercle. The labial goniometer may be used to measure labial/lip droop on either the right or left labial/facial areas. The reference line on the straight edge shank is used to measure the degree of facial droop as indicated on the flared shank by adjusting the shank with the double straight edge upward or downward over the degree range from 0° to 30°. This assessment movement follows the labial seal line to the relaxed labial corner, right or left, of the patient. The measurement of labial/facial flaccidity can be made on the right and on the left side of the patient's labial facial area.

DETAILED DESCRIPTION OF THE OF THE INVENTION

Throughout the following detailed description, the reference numerals refer to those numerals shown in FIG. 1, a drawing of the labial goniometer. The design of the labial goniometer is composed of two flat shanks which are joined in the middle with a grommet 10 which acts as a pivot point. The pivot point allows the shanks to rotate relative to one another. One shank of the labial goniometer 11 has a double flare/straight edge design and the other shank 12 has a double straight edge design along its complete length.

On the shank with the flare design, one longitudinal end 13 has a straight edge design on each side of the shank and the other end 14 is double flared and has a concave curvature on each side of the shank. The flare side and the straight edge side make up about fifty percent of the total length of the shank each. The side of the shank that has a straight edge design is straight on both sides of the shank and is rounded at the end. On the end with the flare design, each flare segment is calibrated in degrees 15, over the range of zero to thirty degrees, above and below a middle reference centerline 16 that runs longitudinally along the entire length of the shank. The degree ranges are progressive in increments of one degree which provides for accurate measurements of labial/lip flaccidity. The design allows for a total measurement of sixty degrees, thirty degree measured movement from the centerline of the flared shank in either direction of rotation from the pivot point. The side of the shank that is flared on both sides has a circular curve 17 on the end like a segment of a circle. The shank with the double straight edge along its complete length also has a reference centerline 18 that runs longitudinally along the shank. Both longitudinal ends of this shank are rounded 19.

The curved portion of the flared shank is placed, with a patient sitting vertically erect, horizontally along the labial/ lip seal line directly under the upper lip tubercle and in a perpendicular position to the philtrum. The patient is to have lips closed and in a resting/relaxed position. The labial goniometer's circular grommet should be in direct alignment to the patient's central philtrum, but under the upper lip tubercle. By moving the straight edge shank upward or downward, whichever is appropriate, the straight edge reference line intersects a degree measurement on the flared segment, which is the result of the reference line following the relaxed labial/lip seal line to the flaccid lip corner. By adjusting the shank with the double straight edge upward or downward, whichever is appropriate, over the degree range from 0° to 30°, a measurement for flaccidity is obtained. This assessment movement follows the labial seal line to the relaxed labial corner of the patient. The measurement of labial/facial flaccidity over a range of 60 degrees, can be made on the right side and on the left side of the patient's labial facial area.

The labial goniometer can be made out of any transparent type material such as glass or plastic. Alcohol or any bacterial cleansing agent may be used by the professional for sterilization of the goniometer between use on different patients for the purposes of infection control. Imprinting of the labial goniometer is done by silk screening or any other appropriate method. Total dimensions of a normal goniometer are as follows; length of 6.5 inches, width 0.5 inches, with a flared segment width of 1.25 inches, and a thickness of 0.0625 to 0.125 inches.

While in the foregoing specification, this invention has been described in relation to certain preferred embodiments thereof, and many details have been set forth for purposes of illustration, it will be apparent to those skilled in the art that the invention is susceptible to additional embodiments, and that certain of details described herein can be varied considerably without departing from the basic principles of the invention.

Having thus described the invention, what is claimed and desired to be secured by Letters Patent is:

1. A method for measuring labial/facial flaccidity, commonly known as a labial/lip, or facial droop, of patients who have suffered neuromuscular impairment as a result of a stroke, or other impairing diseases which affect the labial/facial neuromuscular integrity comprising:

a. the design of a labial goniometer being composed of two shanks which are joined in the middle with a grommet which acts as a pivot point allowing shanks to rotate relative to one another; one shank of the labial goniometer having a double flare/straight edge design and the other shank having a double straight edge design along its complete length; on the shank with the flare design, one longitudinal end having a straight edge design on each side of the shank and the other end being flared and having a concave curvature on each side of the shank, and on the end with the flare design, each flare segment being calibrated in degrees, over the range of zero to thirty degrees, above and below a middle reference centerline that runs longitudinally along the entire length of the shank, with the degree ranges being progressive in increments of one degree for a total measurement of sixty degrees, thirty degree measured movement from the centerline of the flared shank in either direction of rotation from the pivot point; the shank with the double straight edge along its complete length also having a reference centerline that runs longitudinally along the shank;

b. the curved portion of the flared shank is placed, with a patient sitting vertically erect, horizontally along the labial/lip seal line directly under the upper lip tubercle and in perpendicular position to the philtrum; the patient is to have lips closed and in a resting/relaxed position; the labial goniometer's circular grommet should be in direct alignment to the patient's central philtrum, but under the upper lip tubercle; by moving the straight edge shank upward or downward, whichever is appropriate, the straight edge reference line intersects a degree measurement on the flared segment, which is the result of the reference line following the relaxed labial/lip seal line to the flaccid lip corner; by adjusting the shank with the double straight edge upward or downward, whichever is appropriate, over the degree range from 0° to 30°, a measurement for flaccidity is thus obtained; this assessment movement follows the labial seal line to the relaxed labial corner of the patient; the measurement of labial/facial flaccidity over a range of 60 degrees, can be made on the right side and on the left side of the patient's labial facial area.

2. A method in accordance with claim 1 wherein the labial goniometer is constructed from a materials class consisting of transparent glass or plastic, and more preferably transparent plastic.

3. A method as in claim 1 wherein a degree of measurement of the angle of a patient's labial facial area is in the range of 20 to 45 degrees in either direction from the vertical and more preferably 30 degrees in either direction from the vertical.

4. A method as in claim 1 wherein the progressive degree of measurement of the angle of the patient's labial facial area is in the range of 0.5 to 2.0 degrees, and more preferably one degree.

5. A method as in claim 1 wherein the measurements of the labial goniometer consists of a length of 6.5 inches, a width 0.5 inches, with a flared segment width of 1.25 inches, and a thickness of 0.0625 to 0.125 inches.

* * * * *